(12) United States Patent
Maynard et al.

(10) Patent No.: US 6,944,487 B2
(45) Date of Patent: Sep. 13, 2005

(54) DETERMINATION OF PH INCLUDING HEMOGLOBIN CORRECTION

(75) Inventors: John D. Maynard, Albuquerque, NM (US); Shonn P. Hendee, Albuquerque, NM (US); Mark R. Rohrscheib, Albuquerque, NM (US); David Nunez, Albuquerque, NM (US); M. Kathleen Alam, Cedar Crest, NM (US); James E. Franke, Franklin, TN (US); Gabor J. Kemeny, Madison, WI (US)

(73) Assignee: InLight Solutions, Inc., Albuquerque, NM (US)

( * ) Notice: Subject to any disclaimer, the term of this patent is extended or adjusted under 35 U.S.C. 154(b) by 0 days.

(21) Appl. No.: 10/786,662

(22) Filed: Feb. 25, 2004

(65) Prior Publication Data

US 2004/0181131 A1 Sep. 16, 2004

Related U.S. Application Data

(60) Provisional application No. 60/450,016, filed on Feb. 25, 2003.

(51) Int. Cl.$^7$ ................................................. A61B 5/00
(52) U.S. Cl. ...................... 600/322; 600/310; 600/473
(58) Field of Search ................................. 600/322, 310, 600/320, 323, 328, 473, 475

(56) References Cited

U.S. PATENT DOCUMENTS

| | | | | |
|---|---|---|---|---|
| 5,355,880 A | * | 10/1994 | Thomas et al. | 600/326 |
| 5,792,050 A | | 8/1998 | Alam et al. | 600/310 |
| 5,885,212 A | * | 3/1999 | Scharlack | 600/322 |
| 6,178,346 B1 | * | 1/2001 | Amundson et al. | 600/473 |
| 2003/0109772 A1 | * | 6/2003 | Mills | 600/310 |

OTHER PUBLICATIONS

J. Todd Kuenstner and Karl H. Norris, *Spectrophotometry of Human Hemoglobin in the Near Infrared Region from 1000 to 2500 nm*; J. Near Infrared Spectroscopy 2, 59–65 (1994).

David M. Haaland and Edward V. Thomas, *Partial Least-Squares Methods for Spectral Analyses 1. Relation to Other Quantitative Calibration Methods and the Extraction of Qualitative Information*; Anal. Chem., 60, pp. 1193–1202 (1988).

M. Kathleen Alam, Mark R. Rohrscheib, James E. Franke, Thomas M. Niemczyk, John D. Maynard, and M. Ries Robinson, *Measurement of pH in Whole Blood by Near–Infrared Spectroscopy*; Applied Spectroscopy vol. 53, No. 3, pp. 316–324 (1999).

M. Kathleen Alam, James E. Franke, Thomas M. Niemczyk, John D. Maynard, Mark R. Rohrscheib, M. Ries Robinson, R. Philip Eaton, *Characterization of pH Variation in Lysed Blood by Near–Infrared Spectroscopy*; Applied Spectroscopy, vol. 52, No. 3, pp. 393–399 (1998).

Songbiao Zhang, Babs R. Soller, Ronald H. Micheels, *Partial Least–Squares Modeling of Near–Infrared Reflectance Data for Noninvasive in Vivo Determination of Deep–Tissue pH*; Applied Spectroscopy, vol. 52, No. 3, pp. 400–406 (1998).

Songbiao Zhang, Babs R. Soller, Shubjeet Kaur, Kristen Perras, Thomas J. Vander Salm, *Investigation of Noninvasive in Vivo Blood Hematocrit Measurement Using NIR Reflectance Spectroscopy and Partial Least–Squares Regression*; Applied Spectroscopy, vol. 54, No. 2, pp. 294–299 (2000).

M. Kathleen Alam, James E. Franke, Mark R. Rohrscheib, David Nunez, Vincent Abate, John D. Maynard, Gabor J. Kemeny, *Hemoglobin Correction for Near Infrared pH Determination in Lysed Blood Solutions*; Applied Spectroscopy, vol. 57, 1093–1099 (2003).

* cited by examiner

*Primary Examiner*—Eric F. Winakur
*Assistant Examiner*—Matthew Kremer
(74) *Attorney, Agent, or Firm*—V. Gerald Grafe

(57) ABSTRACT

Methods and apparatuses of determining the pH of a sample. A method can comprise determining an infrared spectrum of the sample, and determining the hemoglobin concentration of the sample. The hemoglobin concentration and the infrared spectrum can then be used to determine the pH of the sample. In some embodiments, the hemoglobin concentration can be used to select an model relating infrared spectra to pH that is applicable at the determined hemoglobin concentration. In other embodiments, a model relating hemoglobin concentration and infrared spectra to pH can be used. An apparatus according to the present invention can comprise an illumination system, adapted to supply radiation to a sample; a collection system, adapted to collect radiation expressed from the sample responsive to the incident radiation; and an analysis system, adapted to relate information about the incident radiation, the expressed radiation, and the hemoglobin concentration of the sample to pH.

25 Claims, 9 Drawing Sheets

US 6,944,487 B2

DETERMINATION OF PH INCLUDING HEMOGLOBIN CORRECTION

REFERENCES TO RELATED APPLICATIONS

This application claims priority under 35 U.S.C. § 120 to U.S. patent application Ser. No. 60/450,016, "Analyte Determination Using Hemoglobin Information," filed Feb. 25, 2003, incorporated herein by reference.

FIELD OF THE INVENTION

The present invention generally relates to the determination of pH in blood, and more specifically to the use of hemoglobin information in the determination.

BACKGROUND OF THE INVENTION

The measurement of blood pH, as part of the suite of measurements known as ABG or arterial blood gases, is considered a critical parameter in assessing the respiratory and metabolic status of the critical care patient. The pH measurement is important for diagnosing the underlying etiology of patient acid-base imbalances. It is also critical for monitoring critical care patients who are either candidates for or are receiving ventilatory assistance.

Current approaches for measuring blood pH require removal of a blood sample from the patient. The sample is typically analyzed using a clinical blood gas analyzer that employees standard potentiometric methods. Clinical blood gas analyzers are complex instruments that require frequent maintenance in the form of cleaning and calibration, and are subject to periods of inoperability due to formation of blood clots in the sample path and/or sensor calibration failure.

Because acid-base status can change rapidly in the critically ill patient, it is often desirable to obtain frequent blood gas measurements to monitor the patient. In many cases it is desirable to obtain continuous or near-continuous information regarding patient acid-base status. However, the invasiveness of acquiring blood samples as well as the progressive blood loss associated with blood sample collection limits the frequency with which the measurement can be made.

A noninvasive method for measuring blood pH would offer numerous improvements over existing methods. It would allow for continuous measurement of a patient's acid-base status, eliminate patient blood loss associated with blood pH measurement, reduce exposure of medical staff to biohazardous material, and reduce the patient pain and morbidity associated with blood draws. It has been demonstrated that blood pH can be measured using near-infrared spectroscopy. See, e.g., M. K. Alam, J. E. Franke, T. M. Niemczyk, J. D. Maynard, M. R. Rohrscheib, M. R. Robinson, R. P. Eaton, Appl. Spec. 52, 393 (1998); M. Alam, M. Rohrscheib, J. Franke, T. Niemczyk, J. Maynard, M. Robinson, Appl. Spec. 53, 316 (1999), each of which is incorporated be reference. Accuracy of the measurement can be important to the proper care of the patient, and previous spectroscopic measurements have not conclusively demonstrated sufficient accuracy.

Accordingly, there is a need for improvements in methods and apparatuses useful in making spectroscopic measurements of blood pH.

SUMMARY OF THE INVENTION

The present invention comprises a method of determining the pH of a sample. The method can comprise determining an infrared spectrum of the sample, and determining the hemoglobin concentration of the sample. The hemoglobin concentration and the infrared spectrum can then be used to determine the pH of the sample. In some embodiments, the hemoglobin concentration can be used to select an model relating infrared spectra to pH that is applicable at the determined hemoglobin concentration. In other embodiments, a model relating hemoglobin concentration and infrared spectra to pH can be used.

The present invention is useful for determining the pH of samples such as a blood sample drawn from a patient; a blood sample measured intravascularly (indwelling measurement); perfused tissue; perfused skin; an ex vivo blood sample in a transmission vessel; an ex vivo blood sample in a transflectance vessel; a blood sample in an on-line flow circuit; in situ measurement of a perfused tissue; and in situ measurement of a perfused organ or muscle. The infrared spectrum can be, as examples, measurements of the sample absorbance of infrared radiation using transmission, diffuse reflectance, transflectance, or ATR methods.

The present invention further comprises apparatuses suitable for determining the pH of a sample. An apparatus according to the present invention can comprise an illumination system, adapted to supply radiation to a sample; a collection system, adapted to collect radiation expressed from the sample responsive to the incident radiation; and an analysis system, adapted to relate information about the incident radiation, the expressed radiation, and the hemoglobin concentration of the sample to pH.

BRIEF DESCRIPTION OF THE DRAWINGS

The drawings, which are not necessarily to scale, depict illustrative embodiments and are not intended to limit the scope of the invention.

DETAILED DESCRIPTION OF THE INVENTION

Figure 1A:
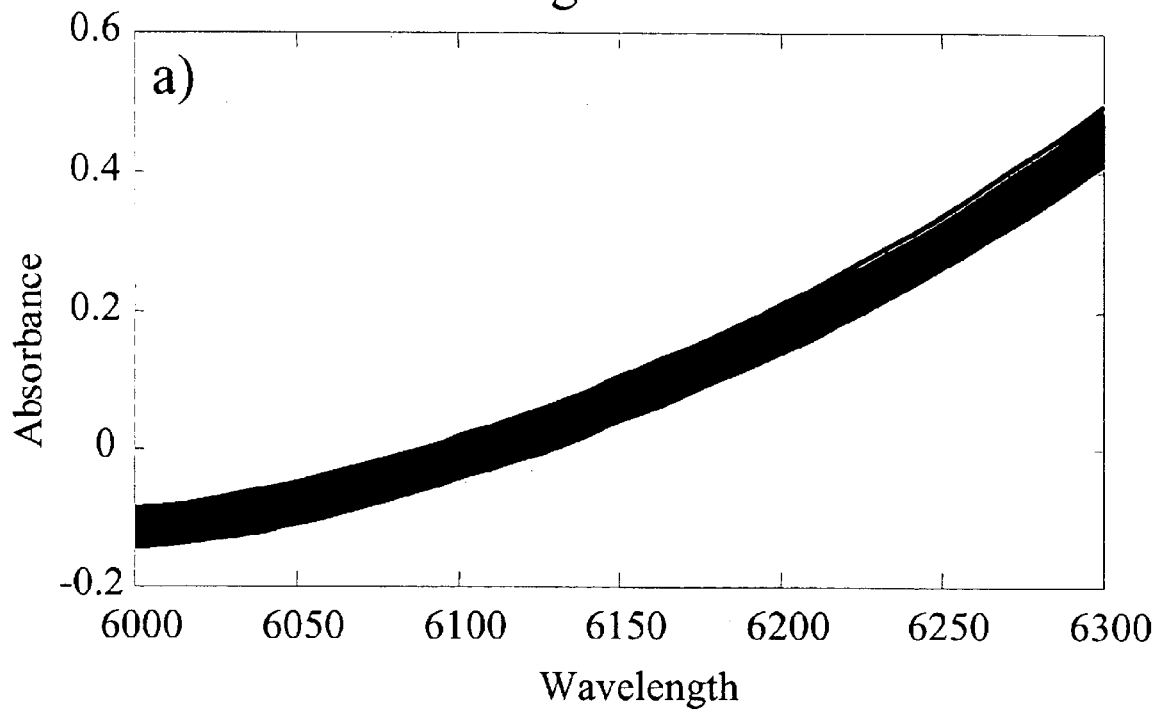
FIG. 1a is an illustration of 255 absorbance spectra of blood bead solutions, containing pH, Hb, pCO2 and [HCO3-] variation.

Near infrared (NIR) measurement of blood pH can use the spectral signature of histidine residing on the hemoglobin molecule. If the amount of hemoglobin in solution varies, the size of the histidine signal can vary depending on changes in either pH or hemoglobin concentration. See, e.g., M. K. Alam, J. E. Franke, M. R. Robinson, D. Nunez, V. Abate, J. D. Maynard, G. J. Kemeny, "Hemoglobin Correction for Near-infrared pH Determination in Lysed Blood Solutions,", Appl. Spec. 57, 1093 (2003). Multivariate calibration models, developed using the NIR spectra collected from blood at a single hemoglobin concentration, can predict data from blood samples of different hemoglobin levels with a bias and slope. A simple, scalar path length correction of the spectral data can be inadequate to correct this problem. However, global multivariate models built with data encompassing a range of hemoglobin concentration can have a cross-validated standard error of prediction (CVSEP) similar to the CVSEP of data obtained from a single hemoglobin level. The prediction of pH of an unknown sample using a global multivariate model can require that the unknown have a hemoglobin concentration falling within the range encompassed by the global model. An alternative method for predicting blood pH can use a model built from samples with a narrow range of hemoglobin levels and then applies a correction to the measurement based on a separate determination of the hemoglobin concentration using an equation developed to correct predicted pH values. Since both methods require some knowledge of the hemoglobin concentration order for a pH prediction to be made, a model for determining hemoglobin concentration using data from the same spectral region is also presented.

A method according to the present invention can comprise determining a near-infrared spectrum of a sample. A near-infrared spectrum generally refers to any illumination/response relationship, and can be, as examples, transmission, transflectance, diffuse reflectance, attenuated total reflection, and other relationships appreciated by those skilled in the art. The near infrared spectrum can consist, for example, of wavelengths in the range from 4000 to 15,000 cm−1. A sample can comprise, as examples, blood samples removed from a patient, intravascular blood, skin, or other perfused tissue. The concentration of hemoglobin can be determined, for example by an external measurement, or by determination from the infrared spectrum. There are other parameters related to the concentration of hemoglobin which can be used instead, for example hematocrit. For convenience, the description herein refers to the concentration of hemoglobin, which term includes other parameters related to, derivable from, or useful in the derivation of the concentration of hemoglobin. The determined hemoglobin concentration can be used to select a model relating infrared spectra to pH, where the model is applicable for a range of hemoglobin concentrations that spans the determined hemoglobin concentration. The model can then be used with the infrared spectrum to determine the pH of the sample. Inaccurate hemoglobin concentration can affect the accuracy of the pH determination, so in some embodiments it can be useful to measure the sample hemoglobin concentration under physiological conditions that are not undergoing rapid change (e.g., during substantial blood loss or during rapid administration of intravascular fluids), and to account for errors introduced by potentially interfering intravascular substances (e.g., blood substitutes or cardiovascular dyes).

A method according to the present invention can comprise determining an infrared spectrum of a sample. The concentration of hemoglobin can be determined, for example by an external measurement, or by determination from the infrared spectrum. The determined hemoglobin concentration can be used as an input to a model that relates infrared spectra and hemoglobin concentration to pH, where the model is applicable to a range of hemoglobin concentrations that includes the determined value. The sample can comprise a variety of configurations, examples including a blood sample drawn from the patient; a blood sample measured intravascularly (indwelling measurement); perfused tissue; perfused skin; an ex vivo blood sample in a transmission vessel (cuvette, capillary tubing, flow cell); an ex vivo blood sample in a transflectance vessel (cuvette, tubing, flow cell); a blood sample in an on-line flow circuit (e.g., dialysis circuit or cardiac bypass system); in situ measurement of a perfused tissue; and in situ measurement of a perfused organ or muscle.

Spectroscopic measurement of pH has been described in U.S. Pat. No. 5,792,050 to Mary K. Alam and Mark R. Robinson, titled "Near-infrared Noninvasive Spectroscopic Determination of pH" (hereinafter "Alam and Robinson"), a continuation of U.S. Pat. No. 5,355,880 issued to Edward V. Thomas, Mark R. Robinson, David M. Haaland and Mary K. Alam titled "Reliable Noninvasive Measurement of Blood Gases" (hereinafter "Thomas et al."), each of which is incorporated herein by reference. Thomas et al. discloses methods and apparatus for determining noninvasively and in vivo at least two of the five blood gas parameters (i.e., pH, $pCO_2$, [HCO3-], $pO_2$, and $O_2$sat) in a human. The noninvasive methodology disclosed includes the steps of: generating light at three or more different wavelengths in the range of 500 nm to 2500 nm; irradiating blood-containing tissue; measuring the intensities of the wavelengths emerging from the blood-containing tissue to obtain a set of at least three spectral intensities v. wavelengths; and determining the unknown values of at least two of pH, [HCO3-], $pCO_2$, and a measure of blood oxygenation. The methodology disclosed also includes the steps of providing calibration samples, determining if the measured spectrum from the tissue represents an outlier, and determining if any of the calibration samples represents an outlier. The determination of the unknown values was performed by at least one multivariate algorithm (e.g., PLS (partial least squares), PCR (principal component regression), and CLS (classic least squares)) using two or more variables and at least one calibration model. Preferably, there is a separate calibration model for each blood gas parameter being determined. The method can be utilized in a pulse mode. The method can also be used invasively or can be used to measure blood gas parameters of blood samples ex vivo. The apparatus disclosed by Thomas et al. includes a tissue positioning device, a source, at least one detector, electronics, a microprocessor, memory, and apparatus for indicating the determined values.

The methodology disclosed by Alam and Robinson teaches that determination of blood pH can be made by using measured intensities at wavelengths that exhibit change in absorbance due to histidine titration. The histidine absorbance changes are due titration by hydrogen ions. Alam and Robinson disclose a quantitative analysis instrument for measuring pH in human tissue that includes: a source of at least three different wavelengths of light, the wavelengths being in the range of 1000–2500 nm and at least some of the wavelengths having a wavelength dependent differential attenuation due to histidine; optics for directing the wavelengths into the blood-containing tissue; at least one detector for measuring the intensity of at least a portion of those wavelengths of light emerging from the blood-containing tissue that are differentially attenuated by histidine; electronics for processing the measured intensities to estimate pH values in tissue; and apparatus for indicating the estimated values of blood pH.

Experimental Result with an Example Embodiment

Since the clinical measurement of blood pH is generally made on intact whole blood, with hemoglobin limited to the erythrocyte intracellular space, blood pH was related to spectra collected from whole blood solutions. See, e.g., M. Alam, M. Rohrscheib, J. Franke, T. Niemczyk, J. Maynard, M. Robinson, Appl. Spec. 53, 316 (1999), incorporated herein by reference. Studies using whole blood successfully modeled blood pH using the near infrared signature of histidine within the hemoglobin molecule. During the course of the whole blood study, two separate whole blood data sets were used as calibration and validation sets. Predictions for pH across these two data sets benefited from adjustments to account for slope and bias. Presumably, the slope and bias errors resulted from differences in hemoglobin concentrations between the two data sets. The slope and bias errors were not unexpected, since the histidine spectral signal that provides pH information is also influenced by the concentration of hemoglobin. Results from a large study in which pH, hemoglobin, and bicarbonate were varied in order to study the effect of hemoglobin variation on the spectral model for pH are presented below.

Experimental Design, Mathematical Modeling

An experimental design was developed using a Latin Hypercube with a D-optimality criterion with pH, bicarbonate ion [HCO3-] and hemoglobin as components. This design provided a nearly orthogonal relationship between the components while allowing more levels for each component relative to a more traditional factorial design. 261 experimental target points were developed. The data collected from six of the samples were found to significantly different from the rest of the data collected, due to problems with the reference measurements, or problems with the spectral data collection. These samples were removed from further analysis. The remaining 255 spectral data samples were analyzed using Partial Least Squares (PLS) modeling, with software developed at Sandia National Laboratories. See, e.g., D. M. Haaland, E. V. Thomas, Anal. Chem. 60, 1193 (1988), incorporated herein by reference. PLS is a quantitative multivariate calibration technique which models the covariance of the spectral intensities with the reference values of the analyte. Other analyses were performed using routines developed with MATLAB (The Mathworks, Natick, Mass.).

By using a nearly orthogonal experimental design, correlation between pH and bicarbonate ion was minimized as much as the physiological limits allowed. The bicarbonate ion concentrations were limited at low pH by the pCO2 range (7–51 mmHg), thus introducing an $R^2$ of 0.46 between pH and bicarbonate ion. Since pO2 was kept at a constant, high value, the calculated O2Sat correlated to the measured pH, producing an $R^2$ of 0.824. As will be discussed, this correlation did not effect the pH model.

Sample Preparation

One unit (450 ml) of heparinized whole blood was collected from a non-smoking, healthy volunteer. The blood was separated into plasma and red cell partitions using a Sorvall centrifuge operating at 3000 rpm for 10 minutes and 4° C. The plasma was stored at 4° C. and set aside for stock solution preparation. A stock solution of lysed blood was prepared by rupturing the cell membranes using a sonicator probe operating at 20 kHz and 50 watts for 1 minute. In order to prevent heating during sonication, solutions were kept in ice water. Cell membranes were removed by spinning the lysed blood solution for 10 minutes at 3000 rpm and 4° C. The resulting pellet, containing the cell walls, was discarded. Supernatant, containing hemoglobin was removed and used for stock solution preparation. The hemoglobin concentration of the resulting supernatant was 14.1 gm/dl, as measured on a Ciba Corning Model 270 Co-Oximeter. Both the resulting hemoglobin solution and serum were stored at 4° C. and used as needed to create five stock solutions.

Five stock solutions with hemoglobin levels ranging from 0.32–1.12 gm/dl were prepared. The resulting hemoglobin concentrations were 0.32, 0.52, 0.72, 0.92 and 1.12 gm/dl. Scattering material, in the form of 0.44-micron polystyrene beads (Bangs Laboratories, Fishers, Ind.), was added to each stock solution such that the final concentration of the beads in each solution was 0.005 gm/ml. The bead concentration was chosen to reflect the scattering seen during transillumination of the forepaw of a Sprague-Dawley rat. Triton X-100 surfactant (0.02 gm/ml) was added to each solution in order to prevent bead coagulation. Plasma made up the remainder of each solution. The resulting stock solutions were stored at 4° C. until needed to prepare each sample.

Each sample in the experimental design was then prepared by adding 0.9 N saline followed by acid (HCl) or base (NaOH) to an aliquot of one of the stock solutions so that the total mass of each sample was approximately 3.05 gm. The amount of acid or base required to reach a given experimental design target was estimated by using the Sigaard-Anderson equation for base excess. Base excess estimates the amount of acid or base needed to titrate one liter of blood to a normal acid/base status, which is pH=7.40, pCO2=40 mmHg, hemoglobin=15 gm/dl, and temperature=37° C.

Following the addition of all components described above, each sample was tonometered in an Instrumentation Laboratories (Model 237) tonometer, for 7 min at 37° C. with a humidified mixture of O2, N2, and CO2. The gas mixtures for the tonometer were set using a Cameron Instruments (Model GF-3) mass flow controller. Following tonometry, the reference values were measured and near infrared spectra were collected.

Description of Flows Apparatus and Spectroscopic Measurement

A flow apparatus was designed to allow the measurement of each sample spectroscopically while holding the temperature (37° C.) and flow rate constant. Stainless steel connections isolated each sample from the external atmosphere as it moved through the flow system. A flow rate of 2 ml/min was chosen to allow 2 minutes of spectral data collection. Data collection from each sample commenced when the in-line optical flow cell (5 mm pathlength) became completely filled with fluid. Between samples, the system was flushed with water, bleach solution, deproteinizer, ethanol and air. See, e.g., M. K. Alam, J. E. Franke, T. M. Niemczyk, J. D. Maynard, M. R. Rohrscheib, M. R. Robinson, R. P. Eaton, Appl. Spec. 52, 393 (1998), incorporated herein by reference.

Spectroscopic Measurement

NIR spectra of the whole blood samples were obtained in transmission through the optical flow cell using a Perkin Elmer 2000 Fourier transform NIR spectrometer. The spectrometer was equipped with a stabilized external quartz-tungsten-halogen source (100 Watt, Oriel) and a TE-cooled extended InGaAs photodetector. Spectra were collected at a resolution of 16 cm−1 over the spectral range 5860–11500 cm−1. The samples were prepared and spectra collected in a random order to avoid possible correlation of run order and instrument drift with any of the design variables.

Reference Measurements

ABG values were measured immediately prior to and immediately after spectroscopic data collection. An aliquot of the sample was injected into a Ciba Corning Model 288 automated blood gas analyzer. Measured parameters were pH, pCO2, pO2, and hemoglobin concentration. Bicarbonate ion concentrations [HCO3-] were calculated from the measured pH and pCO2 levels, while oxygen saturation (O2sat) levels were calculated using the measured pO2 and pH.

Figure 1B:
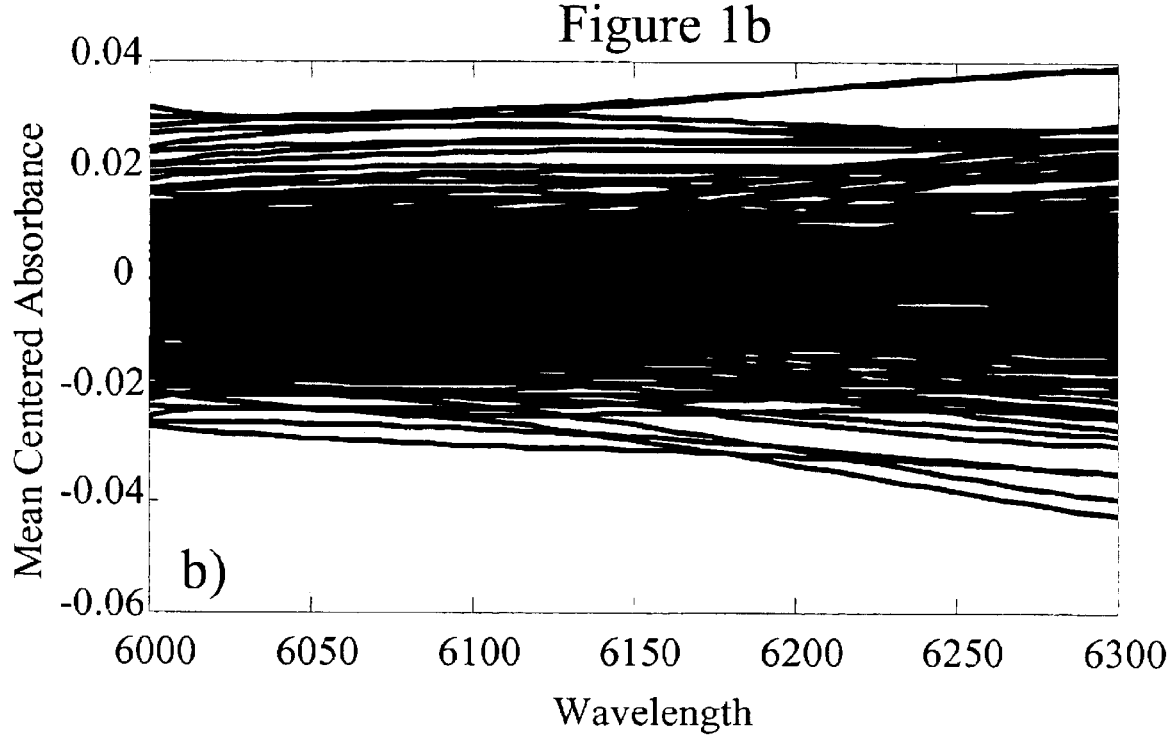
FIG. 1b is an illustration of 255 mean centered absorbance spectra from blood bead solutions, containing pH, Hb, pCO2 and [HCO3-] variation.

Previous work indicated that the prediction of pH using a PLS model created from NIR spectral data at a single hemoglobin level produced slope and bias errors when it was used to predict pH of samples at a different hemoglobin level. This was not surprising, since the NIR pH model has been directly linked to changes in the hemoglobin molecule during titration. The current data, collected from 255 bead-blood samples, allowed the assessment of variable hemoglobin concentration on the pH model. FIG. 1a is an illustration of 255 absorbance spectra of blood bead solutions, containing pH, Hb, pCO2 and [HCO3-] variation. Shown in FIG. 1a are the 255 absorbance spectra collected from the bead-blood data set in the region of interest, 6000 cm-1 to 6300 cm-1. At a resolution of 16 cm-1, each spectrum is composed 41 data points. The baseline variation in FIG. 1a is caused primarily by light scattering from the polystyrene beads. The primary feature in the data shown is the curvature due to the edge of the broad v1+v3 combination band of water centered at approximately 6930 cm-1. See, e. g., K. Buijs, G. R. Choppin, J. Chem. Phys. 39, 2035 (1963), incorporated herein by reference. FIG. 1b is an illustration of 255 mean centered absorbance spectra from blood bead solutions, containing pH, Hb, pCO2 and [HCO3-] variation. Although each sample has one of 5 distinct hemoglobin levels, no clear delineation by hemoglobin level is seen in the mean centered data. The variation present in the mean centered data appears to be random, and is likely due to the slight variation in scatter between each sample from the added beads.

In order to determine whether an unexpected correlation existed between pH and other measured variables, a correlation table was prepared. Table 1 lists the squared correlation coefficients between the measured pH and the other parameters. No significant correlation exists between pH and the variables [HCO3-], pO2 and Hb. A slight correlation ($R^2=0.46$) exists between pH and pCO2. The pCO2 range used in these experiments was chosen based on clinical observations. This clinical range of pCO2 combined with the clinical range of pH will always produce a slight correlation between the two variables. However, since there is no significant signal from CO2 in the NIR, pCO2 variation will not affect the prediction of pH, when NIR spectra are used for modeling.

TABLE 1

| Parameter | Squared Correlation Coefficient |
| --- | --- |
| [HCO$_3$—] | 0.002 |
| PpCO$_2$ | 0.461 |
| PpO$_2$ | 0.061 |
| O$_2$Sat | 0.846 |
| Hb | 0.002 |

There is a significant correlation between the calculated O2Sat and pH. This was not unexpected, since oxygen content was not controlled. Including the correlation due to the Bohr effect can pose difficulties for a pH model created using data collected from the high energy region of the near infrared (14,000–9100 cm-1) due to the extremely strong signal from the electronic transition of the heme. The Bohr effect refers to the change in binding of oxygen to hemoglobin as a result of changes in pH, temperature or pCO2. For instance, if the oxygen content is held constant while pH is decreased, hemoglobin will bind oxygen less strongly, resulting in an effective change in the measured oxygen saturation. Thus pH models built using the visible or high energy near infrared data could inadvertently use the oxyhemoglobin signal. In the longer wavelength near infrared spectral region, signals from oxyhemoglobin are not as large as in the high energy region of the near infrared. See, e. g., J. T. Kuenstner, K. H. Norris, J. Near Infrared Spectrosc. 2, 59 (1994), incorporated herein by reference. pH models containing correlation to oxygen saturation readily predict data containing no correlation between oxygen saturation and pH. Indeed, examination of the resulting loading vectors and regression vectors indicated that models created for pH from correlated and uncorrelated data both contained a distinct pH signature. Thus, for the present experiment, an extremely large experimental design was avoided by not including oxygen saturation variation in the experimental design. Resulting models were examined closely to insure a distinct pH signature was present.

Figure 2:
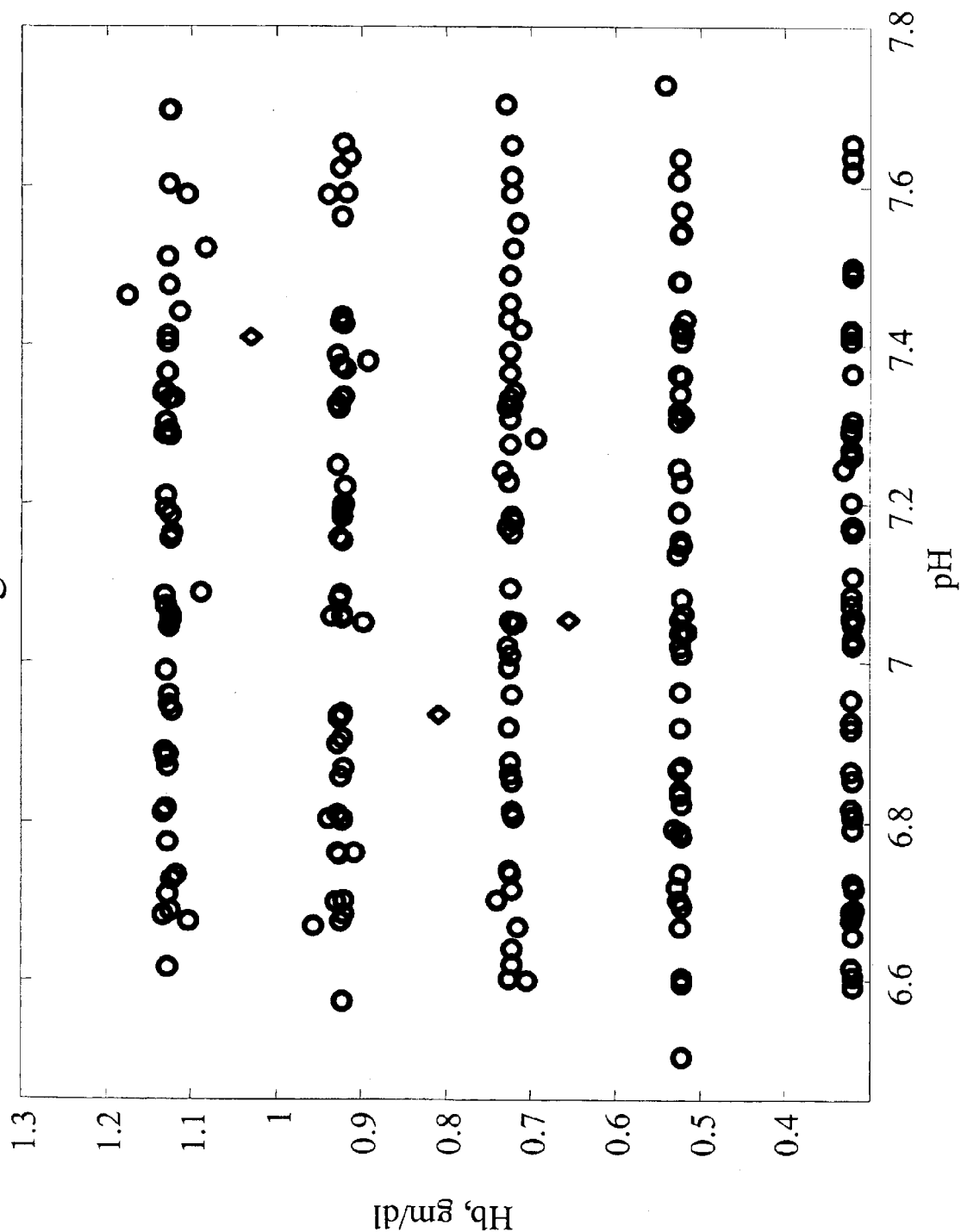
FIG. 2 is a plot of reference pH values versus reference hemoglobin (Hb) values.

FIG. 2 is a plot of reference pH values versus reference hemoglobin (Hb) values. The squared correlation coefficient ($R^2$) between pH and Hb is 0.002. The diamond symbols refer to those points lying outside the five chosen hemoglobin levels. The squared correlation coefficient between pH and Hb is 0.002. The five levels of hemoglobin are readily apparent in the plot. Several points are noted between each of the five levels (diamond symbols, ◊). These intermediate Hb values were not considered 'outliers' in modeling for the entire set. Models created for individual levels indicated that these samples fell outside the model space, since the majority of samples fell within a hemoglobin level, and thus were removed for single hemoglobin level pH modeling.

PLS models for pH were created using data acquired at each hemoglobin level. Results from these analyses are listed in Table 2. The RMS of the CVSEP values for the five sets is 0.030 pH units. See, e.g., M. K. Alam, J. E. Franke, T. M. Niemczyk, J. D. Maynard, M. R. Rohrscheib, M. R. Robinson, R. P. Eaton, Appl. Spec. 52, 393 (1998), incorporated herein by reference; M. Alam, M. Rohrscheib, J. Franke, T. Niemczyk, J. Maynard, M. Robinson, Appl. Spec. 53, 316 (1999), incorporated herein by reference. Work done with lysed blood and whole blood at higher hemoglobin levels achieved model CVSEPs of 0.037 and 0.065 pH units respectively. Since the current data are at much lower hemoglobin levels, it is apparent that the decrease in hemoglobin, and the addition of scatter has not affected the signal-to-noise ratio. The decrease in CVSEP seen in the present data can be due to better environmental controls within the collection time, increased pathlength, and the improved noise characteristics of the instrumentation.

TABLE 2

| Hb level, gm/dl | CVSEP, pH units | # PLS factors |
| --- | --- | --- |
| 0.322 | 0.0315 | 8 |
| 0.524 | 0.0268 | 7 |
| 0.723 | 0.0323 | 7 |
| 0.924 | 0.0201 | 9 |
| 1.12 | 0.0362 | 9 |

Figure 3A:
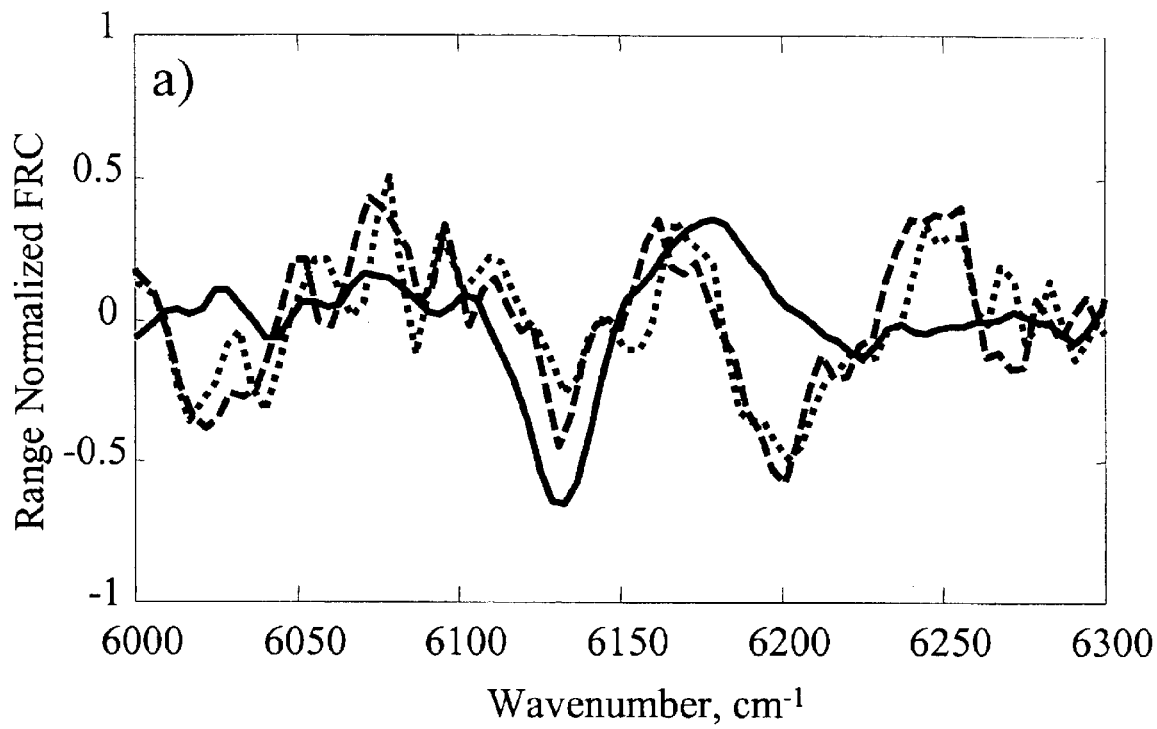
FIG. 3a is a plot of range normalized PLS final regression coefficients (FRCs) from previous data sets.

Since little pO2 variation is present in the data set, the designed pH variations induced a slight variation in O2Sat (range 91–99%) that correlated with blood pH. It can be important to verify that the signal being used in the pH models are indeed related to a pH signal. Previous work indicated that models created from data in which pH was correlated to O2Sat were capable of predicting data in which pH and O2Sat were uncorrelated. To insure the present data models contained pH information, the PLS final regression coefficients (FRCs) from previous data sets were compared to the PLS FRC calculated from the current data. The FRC provides an indication of what features are important to the final model. Using previously collected data, the FRC vector created from data in which pH was not correlated to O2Sat was compared to the FRC vector created from data in which pH and O2Sat were correlated (see FIG. 3a). FIG. 3a is a plot of range normalized PLS final regression coefficients (FRCs) from previous data sets. (- - -) indicates the normalized FRC for the O2Sat model. (···) indicates the range normalized FRC for the pH model built using data in which pH correlated with O2Sat. (●●●) indicates the range normalized FRC for the pH model built using data in which pH did not correlate with O2Sat. The vectors have been normalized for comparison. Common features can be discerned. In particular, note the common feature at 6200 cm−1, identified with pH variation.

Figure 3B:
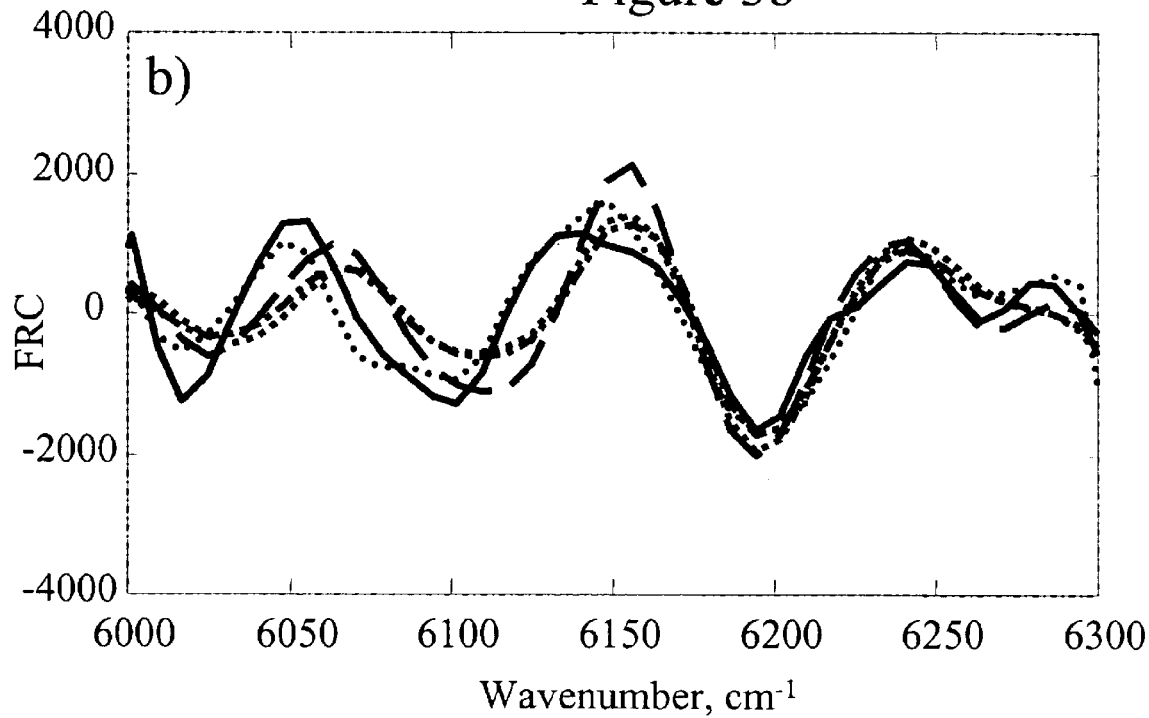
FIG. 3b is an illustration of PLS FRCs from the lysed blood/bead data, one for each hemoglobin level in the study.

An O2Sat model was also determined from the data in which no correlation between O2Sat and pH was present. The squared correlation coefficient for the O2Sat model was 0.87, with a CVSEP of 5.5%, for an O2Sat range of 60–100%. The normalized FRC vector calculated for the O2Sat model is also shown in FIG. 3a. The 6130 cm−1 feature noted in the FRC for O2sat can also be seen in the FRCs calculated for both pH models, yet other features within the O2Sat FRC make it distinct from the pH FRCs. The presence of the O2Sat feature within the pH FRCs did not degrade the predictive capability of the pH model in the presence of O2Sat variation. FIG. 3b is an illustration of PLS FRCs from the lysed blood/bead data, one for each hemoglobin level in the study. (- - -) is the FRC calculated for pH using solutions at Hb=0.32 gm/dl; (■■■)is the FRC calculated for pH using solutions at Hb=0.52 gm/dl; (-■-)is the FRC calculated for pH using solutions at Hb=0.72 gm/dl; (●●●)is the FRC calculated for pH using solutions at Hb=0.92 gm/dl; (-)is the FRC calculated for pH using solutions at Hb=1.12 gm/dl. This figure demonstrates that the feature at 6200 cm−1 is present in all 5 FRC vectors, providing confidence that the present models are focusing on true pH features. The 6130 cm−1 feature, associated with O2sat, is not readily visible in the FRCs calculated for the current data. This is possibly due to differences in resolution between the old and new data, or due to the addition of the scattering beads.

Figure 4:
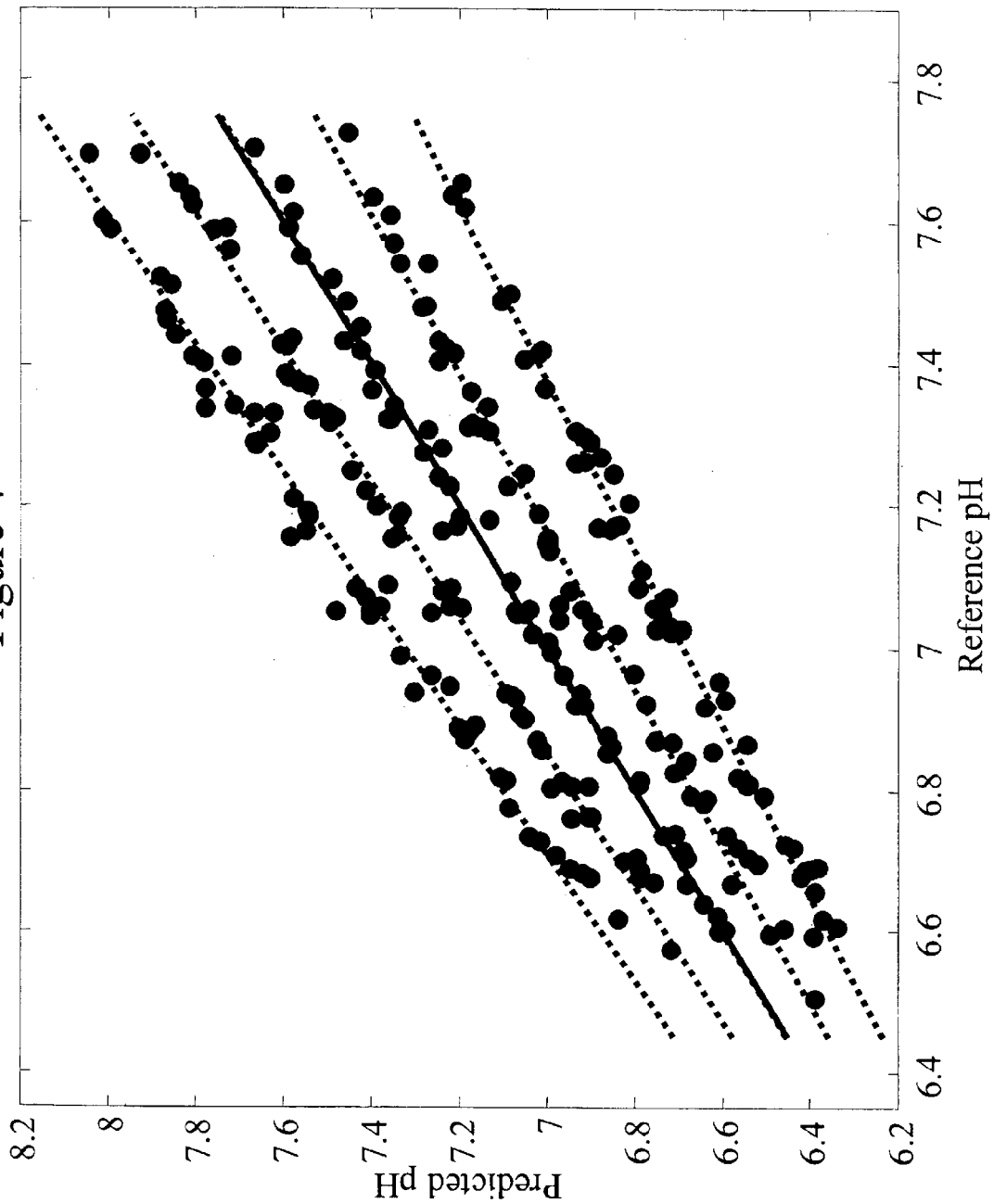
FIG. 4 is a plot of reference pH versus PLS-predicted pH.

Although the FRCs calculated for each hemoglobin level appear similar, slight differences are noted in the size of each FRC, as well in shifts of features between each FRC. Using a single FRC to predict pH data collected at different hemoglobin levels reveals these differences. FIG. 4 is a plot of reference pH versus PLS-predicted pH. The model used for prediction was obtained using samples at Hb=0.72 gm/dl. Distinct slope and intercepts can be seen for each hemoglobin level predicted. Shown in FIG. 4 is a plot of reference pH versus predicted pH using an FRC calculated using pH data obtained at 0.71 gm/dl Hb. Each hemoglobin level is clearly delineated using a least squares fit line. Once the predicted values are adjusted for slope and offset, the pH within each level can be predicted accurately. The slope, offset and the slope- and offset-corrected SEP for each hemoglobin level are listed in Table 3.

TABLE 3

| Hb level of set predicted, gm/dl | Slope | Intercept | Intercept and slope corrected SEP, pH units |
|---|---|---|---|
| 0.322 | 0.824 | 0.92 | 0.0316 |
| 0.524 | 0.899 | 0.56 | 0.0326 |
| 0.723 | 0.996 | 0.05 | 0.0248 |
| 0.924 | 1.05 | −0.22 | 0.023 |
| 1.12 | 1.11 | −0.47 | 0.0396 |

Figure 5:
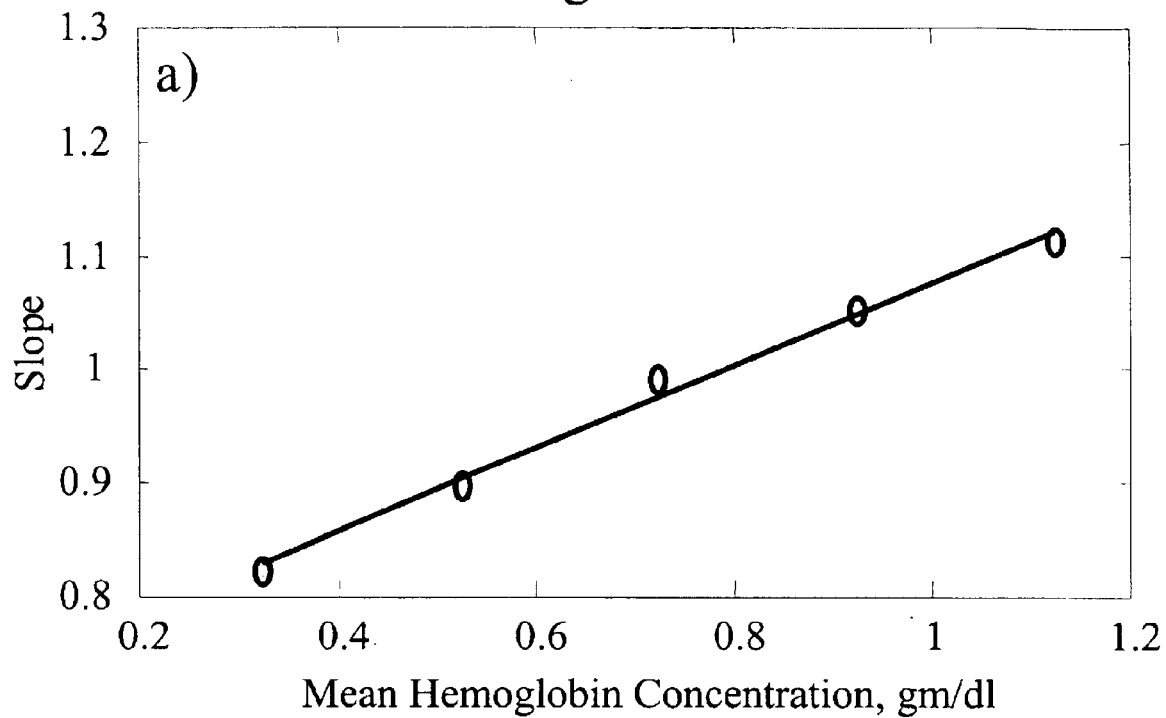
FIG. 5 is a plot of mean hemoglobin concentration.
Figure 5:
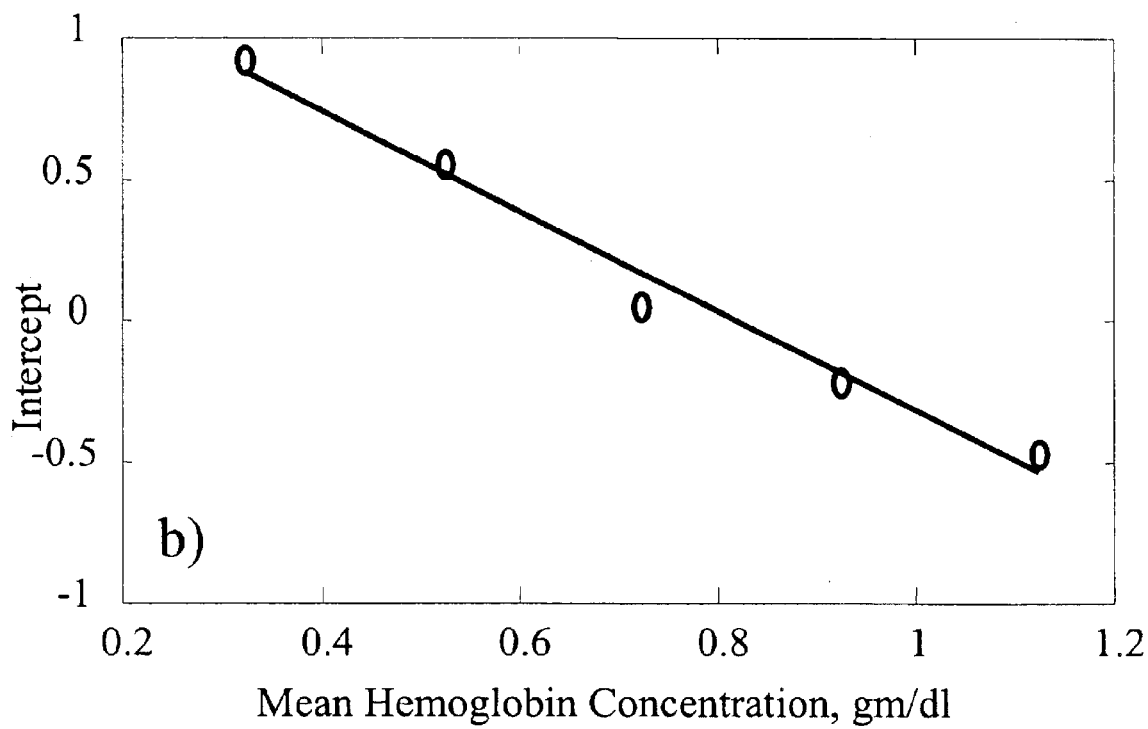

The specificity of a pH model to a hemoglobin level is not surprising, since it was shown previously 1 that the spectroscopic determination of pH in blood solutions is dependent on the titration of hemoglobin. Thus the variation in the amount of hemoglobin will cause a variation in the size of the pH spectral signal. Unfortunately, since both slope and intercept of the predicted values vary with the hemoglobin level, a single scalar correction difficulties not possible. The hemoglobin level is, however, linearly related to both the slope and intercept values listed in Table 3 (see FIGS. 5a and 5b). Using the relationships between the mean hemoglobin level and the slope and intercept values, an equation can be derived that corrects the predicted pH if the hemoglobin level of the sample is known. Equation 1 below is specific to using the 0.71 gm/dl hemoglobin level for prediction, and was used to predict pH at the other four hemoglobin levels.

$$Hb\text{-corrected }pH=[PLS\text{-predicted }pH+(Hb\times1.773-1.452)]/[Hb\times0.365+0.712] \quad (1)$$

Figure 6:
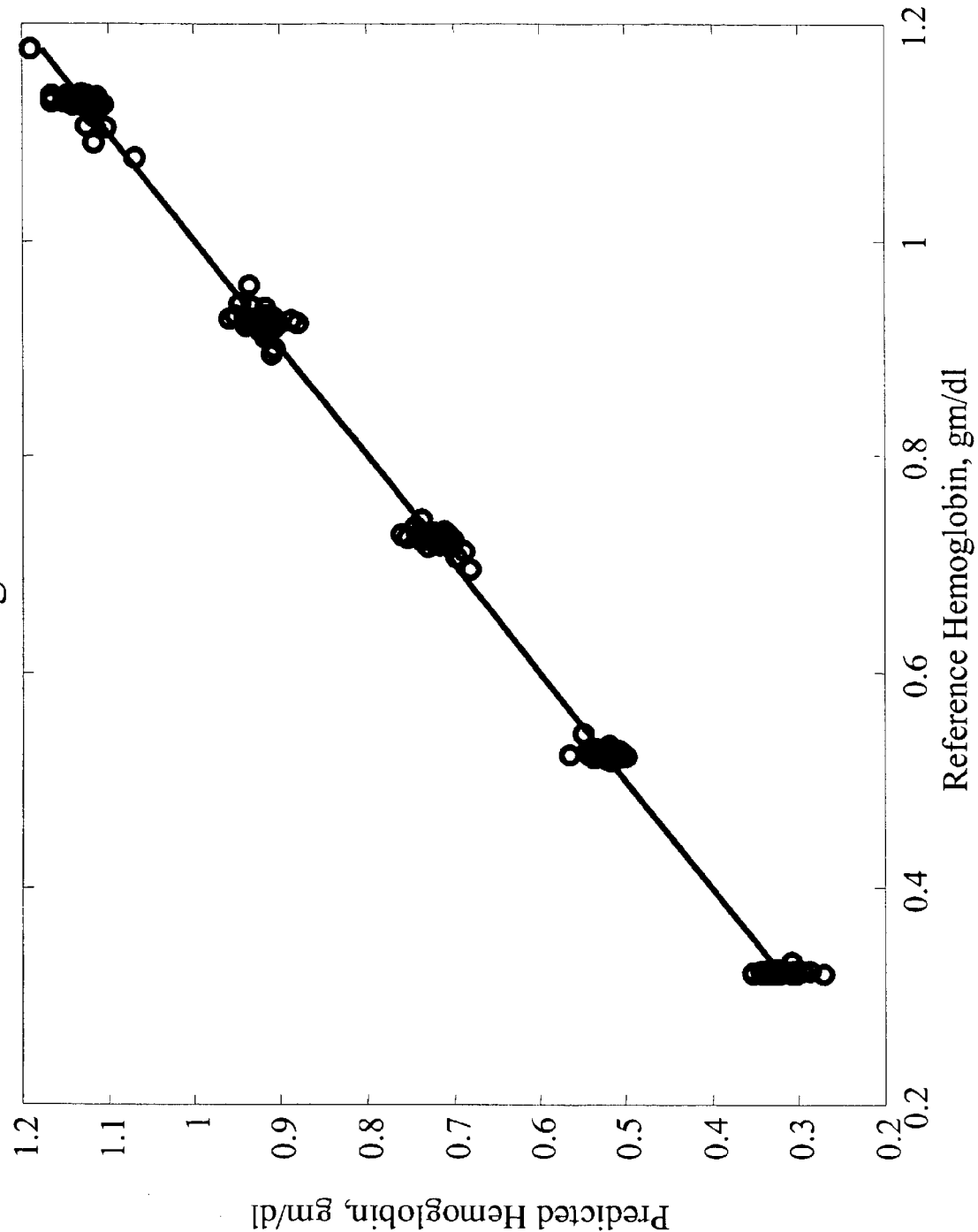
FIG. 6 is a plot of reference hemoglobin concentration versus PLS-predicted hemoglobin concentration, using NIR spectral data.
Figure 7:
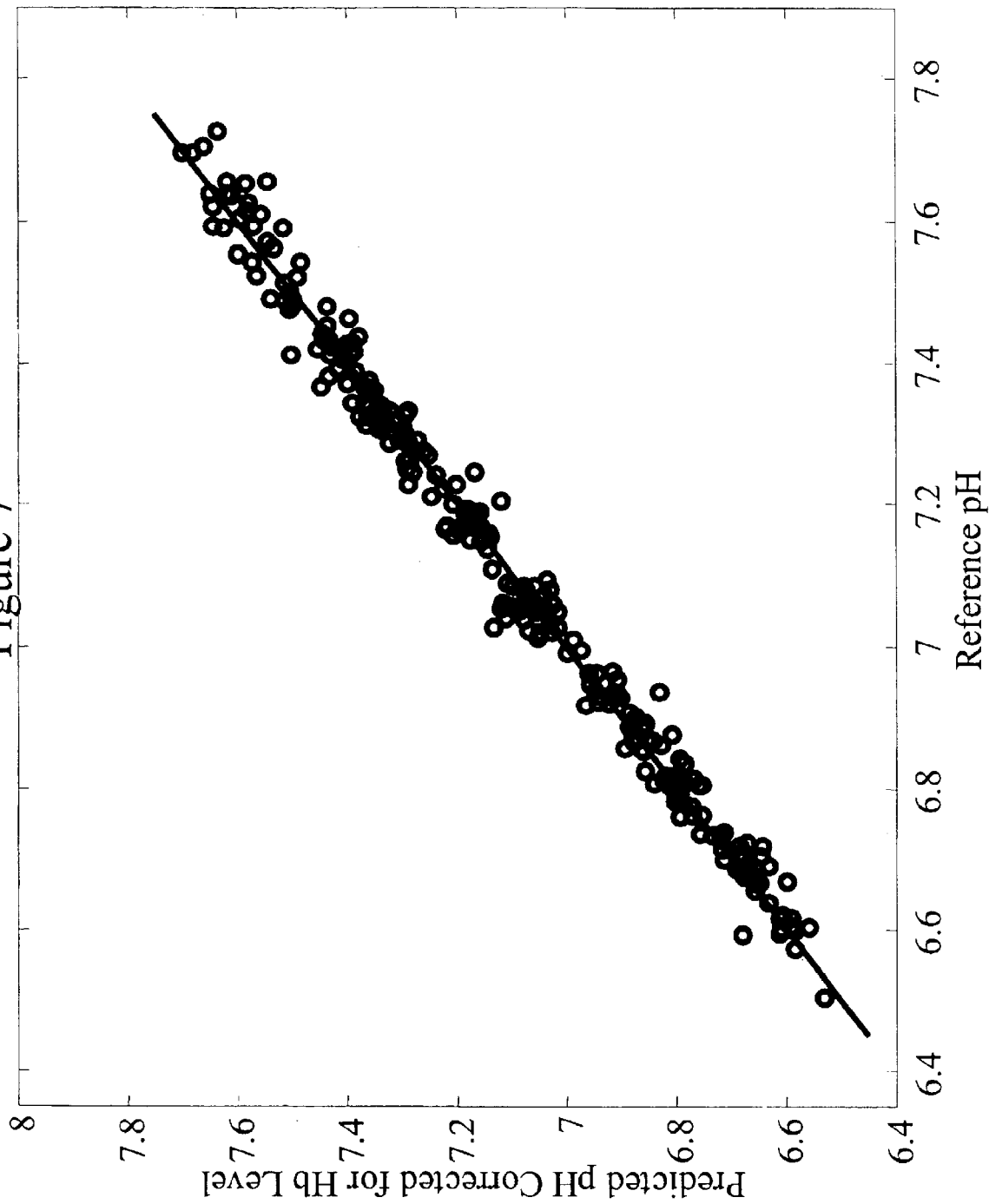
FIG. 7 is an illustration of example results of reference pH versus PLS-predicted pH.

The hemoglobin level of the solution predicted must be known in order for the correction to be applied. Fortunately, the spectral data can also be used to predict hemoglobin level. Combining all the spectral data and building a 10-factor PLS model for hemoglobin using the same spectral region, a CVSEP of 0.0134 gm/dl hemoglobin was achieved, providing an $R^2$ of 0.998. FIG. 6 is a plot of reference hemoglobin concentration versus PLS-predicted hemoglobin concentration, using NIR spectral data. The model for hemoglobin, combined with the above equation and the single hemoglobin level PLS pH model provides a method for predicting pH at alternate hemoglobin levels. The robustness of this method was tested by creating a pH PLS model using data from each hemoglobin level, and creating a correction equation using 4 of the five slope and intercept values from the pH prediction. Each model and equation was used to predict each Hb set not used in the creation of the correction equation. Results are listed in Table 4. Although there is an apparent increase in the pH SEP of the 0.32 and 1.12 gm/dl sets, the SEP values were not significantly different form the SEP values of the other predicted sets ($\alpha=0.001$). Example results of reference pH versus PLS-predicted pH are shown in FIG. 7. The PLS model used to generate the pH predictions shown in FIG. 7 was obtained using samples at Hb=0.71 gm/dl. The predicted values are corrected using equation 1. The Hb-corrected results yielded an SEP of 0.032 pH units. The corrected predictions show marked improvement in accuracy, with an SEP=0.0324 pH units.

TABLE 4

| [Hb] for Set used to build pH model, gm/dl | [Hb] for Set predicted, gm/dl | SEP, pH units | $R^2$ |
|---|---|---|---|
| 0.32 | 0.52 | 0.026 | 0.993 |
|  | 0.72 | 0.030 | 0.991 |
|  | 0.92 | 0.028 | 0.992 |
|  | 1.12 | 0.033 | 0.989 |
| 0.54 | .032 | 0.034 | 0.987 |
|  | 0.72 | 0.036 | 0.986 |
|  | 0.92 | 0.027 | 0.993 |
|  | 1.12 | 0.040 | 0.982 |
| 0.72 | 0.32 | 0.032 | 0.988 |
|  | 0.52 | 0.035 | 0.988 |
|  | 0.92 | 0.028 | 0.993 |
|  | 1.12 | 0.039 | 0.983 |
| 0.92 | 0.32 | 0.039 | 0.983 |
|  | 0.52 | 0.037 | 0.986 |
|  | 0.72 | 0.040 | 0.984 |
|  | 1.12 | 0.040 | 0.985 |
| 1.12 | 0.32 | 0.042 | 0.981 |
|  | 0.52 | 0.036 | 0.987 |
|  | 0.72 | 0.035 | 0.988 |
|  | 0.92 | 0.032 | 0.991 |

Figure 8:
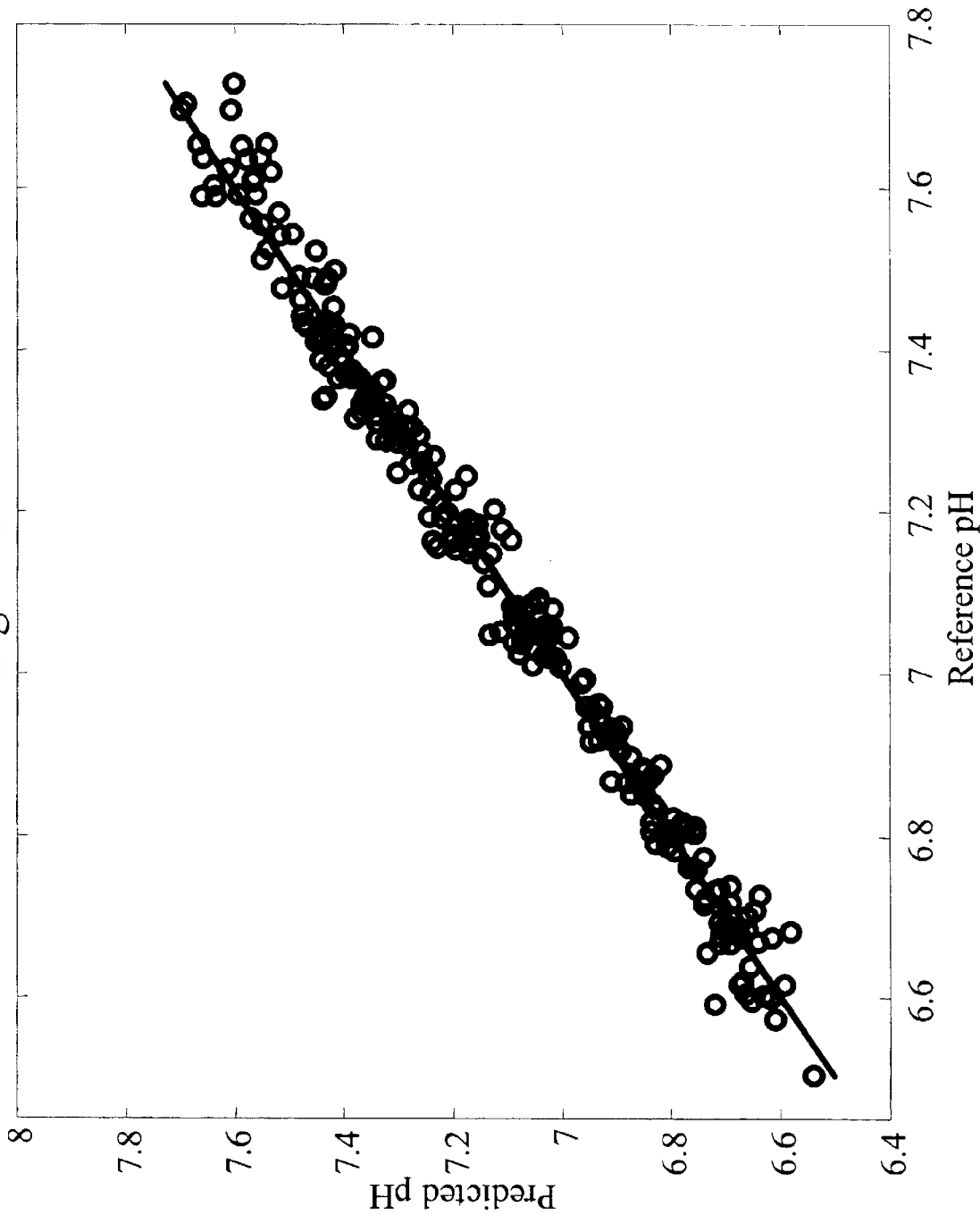
FIG. 8 is a plot of reference pH versus PLS-predicted pH using a global pH model.

Alternatively, a PLS model can be developed using all the spectral data. Using all spectral data, a CVSEP of 0.040 pH units was achieved with a PLS model using 10 factors. The reference versus predicted pH plot obtained using the global model is shown in FIG. 8. FIG. 8 is a plot of reference pH versus PLS-predicted pH using a global pH model. All samples were used to create the 10 factor model. SEP=0.040 pH units. To test the applicability of a global PLS model in the situation where the hemoglobin might not be known, 5 separate PLS models were created, leaving one hemoglobin level out at a time and predicting the remaining level. The results are shown in Table 5. For those pH predictions contained within the hemoglobin model space, the accuracy of the prediction is very good. However, for pH prediction of samples whose hemoglobin values are outside the model space, there is a bias and slope error. By comparing the spectral residuals from the prediction to those from the model, an F-test can be performed. Since computing the degrees of freedom can be difficult, the resulting spectral F-ratios are not used as absolute value for comparison to F-test tables. See, e. g. , D. M. Haaland, E. V. Thomas, Anal. Chem. 60, 1193 (1988), incorporated herein by reference. Rather, the spectral F-ratios can be used as a guide to flag possible outliers within the context of the data being examined.

TABLE 5

| Hb level of Set predicted using other 4 sets | SEP, pH units | $R^2$ |
|---|---|---|
| 0.322 | 0.052 | 0.986 |
| 0.524 | 0.038 | 0.990 |
| 0.723 | 0.032 | 0.989 |
| 0.924 | 0.032 | 0.992 |
| 1.12 | 0.051 | 0.988 |

Figure 9:
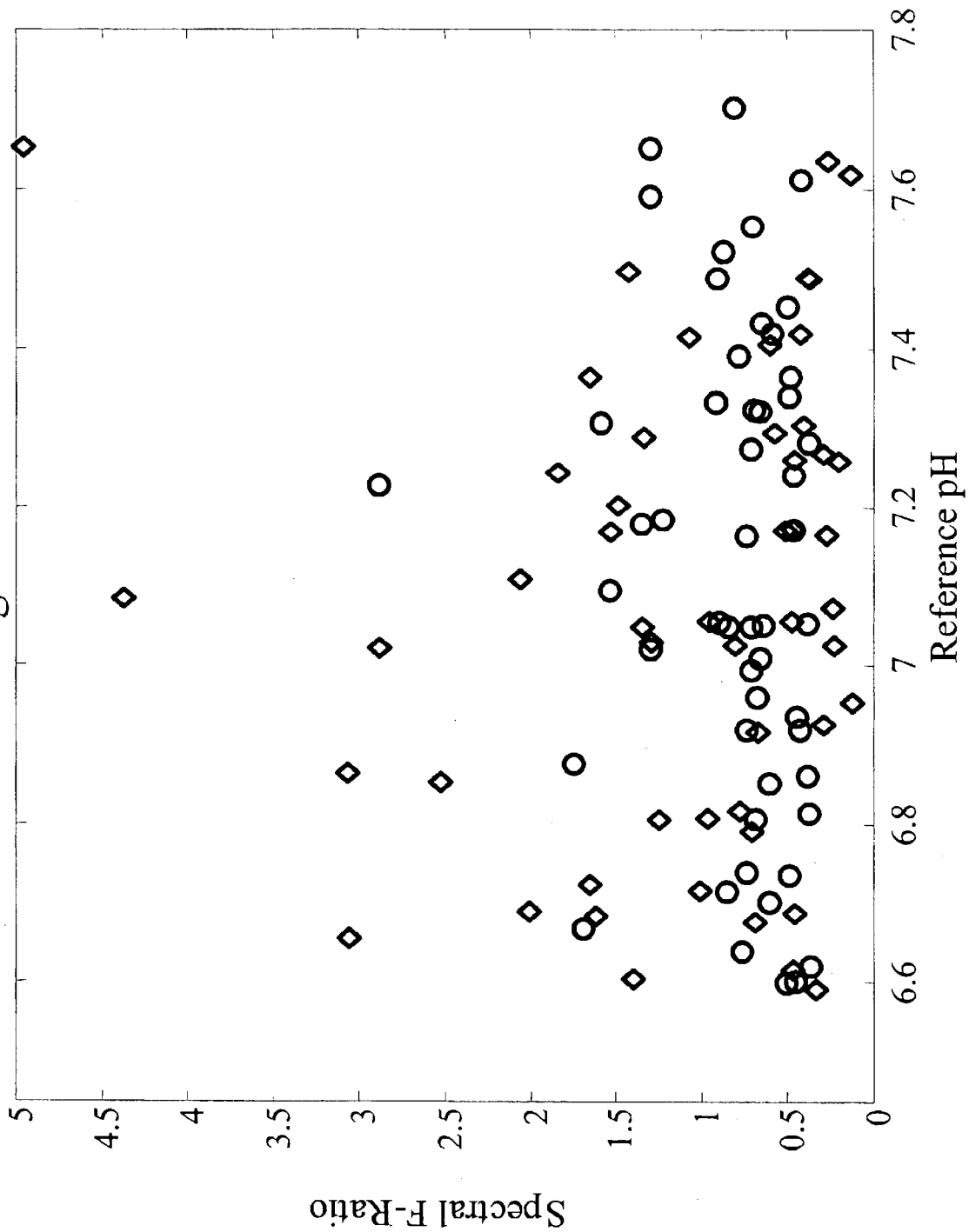
FIG. 9 is an illustration of Spectral F-Ratio values calculated from the prediction of pH.

FIG. 9 is an illustration of Spectral F-Ratio values calculated from the prediction of pH for samples at Hb=0.32 gm/dl using a model containing (◊) samples at 0.52, 0.72, .92, and 1.12 gm/dl Hb, and (○)Spectral F-Ratio values calculated from the prediction of pH for samples at Hb=0.72 gm/dl using a model containing samples at 0.32, 0.52, 0.92 and 1.12 gm/dl Hb. The 0.32 gm/dl samples are outside the hemoglobin concentrations contained in the pH calibration model, however, the Spectral F-Ratio values are not markedly high. FIG. 9 shows the spectral F-ratios from the prediction of the 0.32 gm/dl set using the 0.52, 0.72, 0.92 and the 1.12 sets for model building (◊), as well as the spectral F-ratios from the pH prediction of the 0.72 gm/dl data set using the 0.32, 0.52, 0.92 and the 1.12 gm/dl sets for model building (○). The prediction of the 0.32 gm/dl set did not produce spectral residuals that were severely high, in comparison to the prediction of the 0.72 mg/dl set, which was within the model space. Thus even with the global PLS model, it can be useful to know the hemoglobin level of the predicted sample in order to ensure the hemoglobin of the sample to be predicted is within the model space.

FIG. 4 indicates that a simple correction using a single scalar value is not desirable. This is not unexpected due to the fact that changes in hemoglobin levels induce changes in both the absorption coefficient ($\mu_a$) and the scattering coefficient ($\mu_s$) which in turn change the effective pathlength. The situation is somewhere between simple transmission spectroscopy from non-scattering solutions and complex diffuse reflectance spectroscopy from light-scattering solids. Shorter effective paths occur under strongly absorbing regions of the spectrum relative to weaker absorbing regions because deeper penetrating rays at highly absorbing bands have a greater probability of extinction than do the same-depth rays at weakly absorbing bands. As the hemoglobin concentration increases, $\mu_s$ increases so that the mean free path between scattering events decreases. As a result, deeper penetrating rays at highly absorbing bands have an even greater probability of extinction (as hemoglobin concentration increases) than do the same-depth rays at weakly absorbing bands. These processes lead to an increasingly non-linear spectral response with concentration as $\mu_a$ increases.

At constant hemoglobin concentration, the non-linear response is primarily caused by ma because ma varies significantly with wavelength due to strong water absorption in the NIR region of the spectrum. For that same hemoglobin level, $\mu_s$ is a weak, monotonically varying function with wavelength in the NIR due to the Mie-scattering properties of the particles in solution (size of particles>>wavelength of light). There are some additional spectral non-linearities at very strongly absorbing bands, where ma and ms influence each other due to the correlation of real and imaginary parts of the complex refractive index (Kramers-Kronig relation). However, this additional effect is not significant at most regions of the spectrum. When hemoglobin levels are allowed to vary, only minor changes in water concentration occur so that $\mu_a$ does not change very much. However, $\mu_s$ changes significantly when the hemoglobin levels are changed because the concentration of particles in solution changes significantly. As a result, $\mu_s$ causes the most non-linear spectral responses in the spectrum when hemoglobin concentration is allowed to vary. Given different sources of spectral non-linearities that depend on hemoglobin concentration, it is not unexpected that a PLS pH model trained using data at one hemoglobin concentration would not predict the pH of a sample at a different hemoglobin concentration with precision equal to the original calibration model. In other words, a linear global pH model, such as a PLS model, must include spectral variations coming from multiple hemoglobin levels, and the unknown predicted must be within the model space.

Those skilled in the art will recognize that the present invention can be manifested in a variety of forms other than the specific embodiments described and contemplated herein. Accordingly, departures in form and detail can be made without departing from the scope and spirit of the present invention as described in the appended claims.

What is claimed is:

1. A method of determining the pH of a sample, comprising:
   a) Determining an infrared spectrum of the sample;
   b) Determining the concentration of hemoglobin of the sample;
   c) Selecting a model relating an infrared spectrum to pH that is applicable for samples having the determined hemoglobin concentration;
   d) Determining the pH of the sample from the infrared spectrum and the selected model.

2. A method as in claim 1, wherein the model comprises regression coefficients relating an infrared spectrum to sample pH.

3. A method as in claim 1, wherein the model comprises a model determined from calibration data collected from samples with hemoglobin levels spanning a range of sample hemoglobin levels.

4. A method as in claim 1, wherein the model comprises a model determined from hemoglobin-specific regression coefficients applied to calibration data collected from samples with hemoglobin levels that do not span the sample hemoglobin range.

5. A method as in claim 1, wherein determining an infrared spectrum comprises measuring the sample absorbance of infrared radiation in at least one of transmission, diffuse reflectance, transflectance, and ATR.

6. A method as in claim 1, wherein determining an infrared spectrum comprises measuring the sample absorbance of infrared radiation at a spectral resolution of 64 cm−1 or finer.

7. A method as in claim 1, wherein determining the concentration of hemoglobin comprises at least one of:
   a) Direct measurement of a blood sample using an external instrument or method and;
   b) Spectroscopic measurement of a blood sample.

8. A method as in claim 1, wherein determining the concentration of hemoglobin comprises at least one of:
   a) Measuring the sample hemoglobin concentration under physiological conditions that are not undergoing rapid change and;
   b) Accounting for errors introduced by potentially interfering intravascular substances.

9. A method as in claim 1, wherein the sample comprises at least one of:
   a) A blood sample drawn from the patient;
   b) A blood sample measured intravascularly (indwelling measurement);
   c) Perfused tissue;
   d) Perfused skin;
   e) An ex vivo blood sample in a transmission vessel;
   f) An ex vivo blood sample in a transflectance vessel;
   g) A blood sample in an on-line flow circuit;
   h) In situ measurement of a perfused tissue; and
   i) In situ measurement of a perfused organ or muscle.

10. A method of determining the pH of a sample, comprising:
    a) Determining an infrared spectrum of the sample;
    b) Determining the concentration of hemoglobin of the sample;
    c) Selecting a model relating an infrared spectrum to pH that is applicable for samples having the determined hemoglobin concentration;
    d) Determining the pH of the sample from the infrared spectrum and the selected model;
    wherein determining an infrared spectrum comprises measuring the sample absorbance of infrared radiation in the spectral frequency range from 4000–11000 cm−1.

11. A method as in claim 10, wherein determining an infrared spectrum comprises measuring the sample absorbance of infrared radiation in the spectral frequency range from 4000–8000 cm−1.

12. A method as in claim 11, wherein determining an infrared spectrum comprises measuring the sample absorbance of infrared radiation in the spectral frequency range from 6000–6500 cm−1.

13. A method of determining pH of a sample, comprising:
    a) Determining an infrared spectrum of the sample;
    b) Verifying that the spectrum is spectrally consistent with a model relating an infrared spectrum and associated hemoglobin concentration to pH;
    c) Determining the concentration of hemoglobin, hematocrit, or equivalent of the sample;
    d) Determining the pH of the sample from the infrared spectrum, the determined hemoglobin, hematocrit, or equivalent concentration, and the model.

14. A method as in claim 13, wherein the model comprises regression coefficients relating an infrared spectrum to sample pH.

15. A method as in claim 13, wherein the model comprises a model determined from calibration data collected from samples with hemoglobin levels spanning the range of sample hemoglobin levels.

16. A method as in claim 13, wherein the model comprises a model determined from hemoglobin-specific regression coefficients applied to calibration data collected from samples with hemoglobin levels that do not span sample hemoglobin range.

17. A method as in claim 13, wherein determining an infrared spectrum comprises measuring the sample absorbance of infrared radiation in at least one of transmission, diffuse reflectance, transflectance, ATR.

18. A method as in claim 13, wherein determining an infrared spectrum comprises measuring the sample absorbance of infrared radiation at a spectral resolution of 64 cm−1 or finer.

19. A method as in claim 13, wherein determining the concentration of hemoglobin comprises at least one of:
    a) Direct measurement of a blood sample using an external instrument or method and;
    b) Spectroscopic measurement of a blood sample.

20. A method as in claim 13, wherein determining the concentration of hemoglobin comprises at least one of:
    a) Measuring the sample hemoglobin concentration under physiological conditions that are not undergoing rapid change and;
    b) Accounting for errors introduced by potentially interfering intravascular substances.

21. A method as in claim 13, wherein the sample comprises at least one of:
    a) A blood sample drawn from the patient;
    b) A blood sample measured intravascularly (indwelling measurement);
    c) Perfused tissue;
    d) Perfused skin;
    e) An ex vivo blood sample in a transmission vessel;
    f) An ex vivo blood sample in a transflectance vessel;

g) A blood sample in an on-line flow circuit;

h) In situ measurement of a perfused tissue; and i) In situ measurement of a perfused organ or muscle.

22. A method of determining pH of a sample, comprising:

a) Determining an infrared spectrum of the sample;

b) Verifying that the spectrum is spectrally consistent with a model relating an infrared spectrum and associated hemoglobin concentration to pH;

c) Determining the concentration of hemoglobin, hematocrit, or equivalent of the sample;

d) Determining the pH of the sample from the infrared spectrum, the determined hemoglobin, hematocrit, or equivalent concentration, and the model;

wherein determining an infrared spectrum comprises measuring the sample absorbance of infrared radiation in the spectral frequency range from 4000–11000 cm−1.

23. A method as in claim 22, wherein determining an infrared spectrum comprises measuring the sample absorbance of infrared radiation in the spectral frequency range from 4000–8000 cm−1.

24. A method as in claim 23, wherein determining an infrared spectrum comprises measuring the sample absorbance of infrared radiation in the spectral frequency range from 6000–6500 cm−1.

25. An apparatus for determining the pH of a sample, comprising:

a) An illumination system adapted to direct radiation to the sample;

b) A collection system adapted to receive radiation expressed from the sample responsive to incident radiation;

c) An analysis system, relating two or more of radiation expressed, incident radiation, and hemoglobin concentration to sample pH;

wherein:

d) The infrared radiation encompasses the spectral frequency range between 4000–25000 cm−1;

e) Infrared radiation is delivered to the sample through at least one of: optical fibers, light guides, and imaging optics;

f) Hemoglobin concentration is determined using radiation in the spectral frequency range from 10,000–25,000 cm−1; and g) pH is determined using radiation in the spectral frequency range from 4,000–10,000 cm−1 combined with the hemoglobin concentration.

* * * * *